US00PP07849P

United States Patent [19]

van Andel

[11] Patent Number: Plant 7,849

[45] Date of Patent: Mar. 31, 1992

[54] CARNATION NAMED STATROPUR

[75] Inventor: Jacob van Andel, Aalsmeer, Netherlands

[73] Assignee: Van Staaveren B.V., Aalsmeer, Netherlands

[21] Appl. No.: 611,509

[22] Filed: Nov. 13, 1990

[51] Int. Cl.[5] ..... A01H 5/00

[52] U.S. Cl. ..... Plt./70

[58] Field of Search ..... Plt./70, 72, 73, 70.2, Plt./70.6, 70.7

*Primary Examiner*—Howard J. Locker

*Attorney, Agent, or Firm*—Charles W. Rummler

[57] ABSTRACT

A new and original mini-spray carnation variety particularly distinguished by its bright flat cyclamen-purple blossoms, which are borne profusely and intermittently in clusters on erect stems branching from the main stem of an upright bush that has a height of about 150 cm.

1 Drawing Sheet

BACKGROUND OF THE NEW PLANT

This new mini-spray carnation cultivar originated as a hybrid seedling developed by me at our nursery in Aalsmeer, Holland by crossing two varieties selected from our collection of carnation plants maintained for breeding purposes at Aalsmeer. This particular seedling was selected for propagation because of its unusual flat cyclamen-colored flowers and the overall high quality of the plant growth. Asexual propagation of this selected plant was done by means of cuttings under my direction at Aalsmeer; and propagation of this new plant was continued through successive generations to determine whether the novel characteristics of this selected seedling would be retained from generation to generation and whether its homogeneity could be assured. This proved to be successful and this new mini-spray carnation variety is now being propagated at Aalsmeer.

DESCRIPTION OF THE DRAWING

My new mini-spray carnation cultivar is illustrated by the accompanying full-color photographic drawing, which shows blooming portions of spray stems with buds and flowers in several stages of development, the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Seedling.

Parentage:

*Seed parent.*—*D. Caryophyllus*, unnamed variety (unpatented).

*Pollen parent.*—A Dianthus hybrid resulting from crossing barbatus and an unknown carnation selected from my collection of carnations maintained at Aalsmeer for breeding purposes. (unpatented).

Classification:

*Botanic.*—Dianthus Hybrid.

*Commercial.*—Mini-spray carnation.

Form: Strong, upright bush.

Height: 150 cm, in average.

Main stem:

*Length.*—In average, about 80 cm.

*Growth.*—Strong and upright.

*Branching character.*—Raceme of spaced flowering branches.

Foliage:

*Number of leaves.*—Dependent on season and amount of daylight.

*Leaf size.*—Large.

*Leaf shape.*—Elliptical. Margins: Entire. Texture: Smooth. Color: Upper side — Dark green. Under side — Gray-green.

THE BUD

Size: Medium.

*Diameter.*—Averaging about 3 mm.

*Length.*—Averaging about 20 mm.

Shape: Cylindrical.

Calyx:

*Shape.*—Cylindrical.

*Size.*—Averaging 3 mm in width and 20 mm in length.

*Splitting.*—The calyx does not split.

*Aspect.*—Smooth.

Flower stem:

*Character.*—Erect, strong and upright.

*Color.*—Dark green.

*Length.*—In average, 1 cm.

THE FLOWER

Blooming habit: Intermittent.

Size of flower: Small.

*Diameter.*—Averaging about 30 mm.

*Depth.*—Averaging about 5 mm.

Borne: In a cluster.

Shape when first opening: Flat.

*When mature.*—Flat.

Petalage:

*Number of petals.*—5.

*Texture.*—Soft.

*Appearance.*—Velvety.

*Color.*—Both outer and inside petals: Body: 74 B. Base: White. Reverse Side: White.

Flower stem:

*After full bloom.*—No discoloration.

Persistence: The flowers hang on and dry.

Disease resistance: Resistant to *Fusarium oxysporum,* as observed at Aalsmeer.

Lasting Quality: Averaging about 12 days as a cut flower and 21 days on the plant.

REPRODUCTIVE ORGANS

Stamens: Male, sterile. In general, reproductive organs are absent or rudimental.

Pistils:

*Number.*—2. Styles: Length: 22 mm, in average. Color: White.

*Stigmas.*—Color: White.

Characteristics of ovaries: Normal.

FRUIT

Fertility: The fruit is fertile.

Shape: Cylindrical.

Color at Maturity: Brown.

I claim:

1. The new and distinctive miniature spray carnation plant, substantially as herein shown and described, particularly characterized by its small flat cyclamen-purple flowers, which are produced profusely in clusters on strong, upright branches of the main stem of a strong, tall, upright bush.

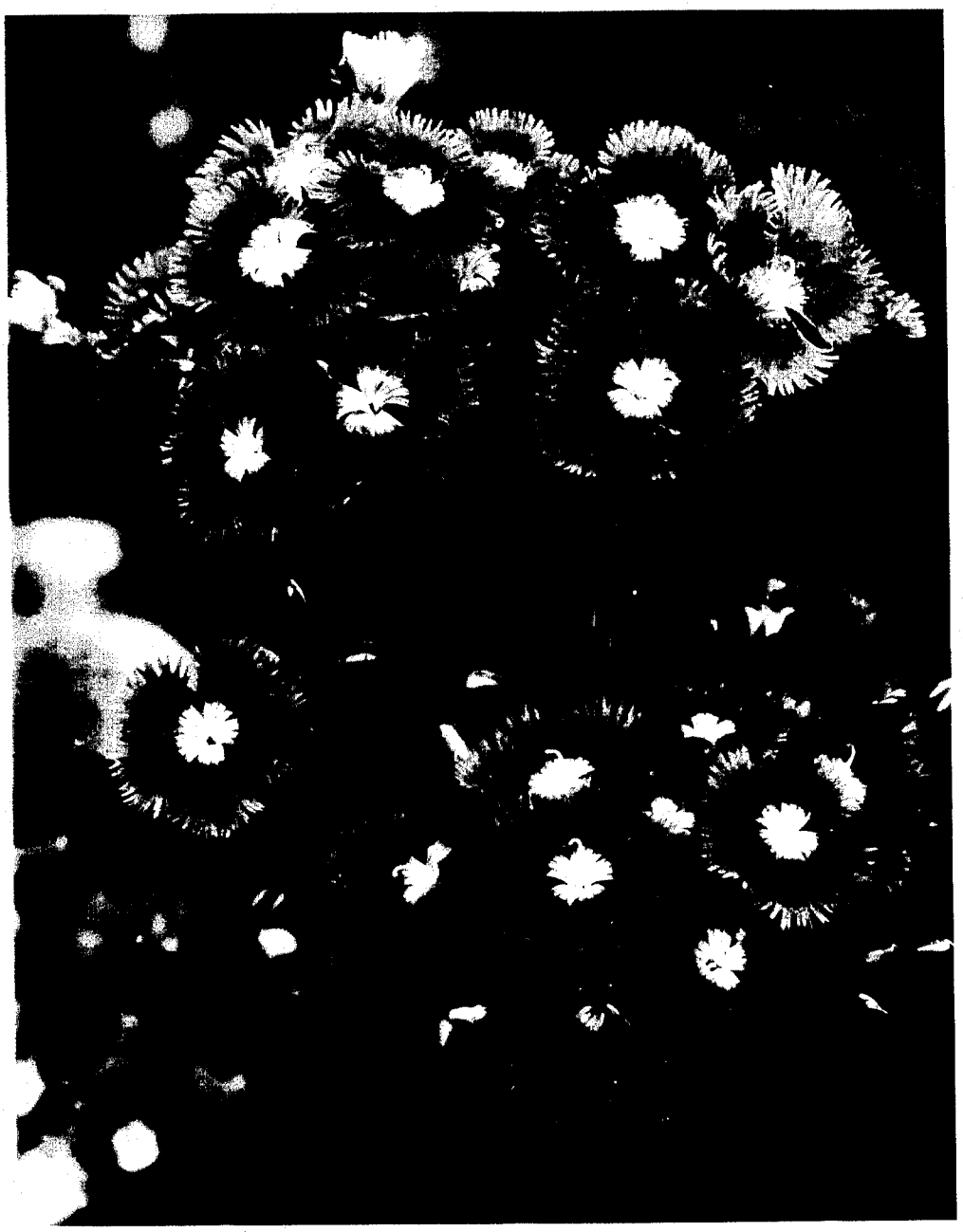

* * * * *